United States Patent

Omid

[11] Patent Number: 5,180,415
[45] Date of Patent: Jan. 19, 1993

[54] PREEMERGENCE WEED CONTROL IN SELECTED CROPS

[75] Inventor: Ahmad Omid, Walnut Creek, Calif.

[73] Assignee: Chevron Chemical Company, San Ramon, Calif.

[21] Appl. No.: 426,473

[22] Filed: Oct. 23, 1989

Related U.S. Application Data

[63] Continuation of Ser. No. 947,006, Dec. 29, 1986, abandoned.

[51] Int. Cl.⁵ ............................................ A01N 43/08
[52] U.S. Cl. .................................. 504/299; 504/176
[58] Field of Search .................................... 71/88

[56] References Cited

U.S. PATENT DOCUMENTS

| | | | |
|---|---|---|---|
| 3,239,538 | 3/1966 | Speziale et al. | 71/88 |
| 4,568,376 | 2/1986 | Ward | 71/88 |
| 4,666,502 | 5/1987 | Seckinger et al. | 71/88 |

FOREIGN PATENT DOCUMENTS

| | | | |
|---|---|---|---|
| 899931 | 12/1984 | Belgium. | |
| 0944570 | 12/1963 | United Kingdom | 71/88 |

OTHER PUBLICATIONS

Ashton, F. M. et al. Mode of Action of Herbicides. New York. John Wiley & Sons, 1981. p. 4–6.

Primary Examiner—Allen J. Robinson
Assistant Examiner—John D. Pak
Attorney, Agent, or Firm—R. C. Gaffney; L. S. Squires

[57] ABSTRACT

A method for providing preemergent weed control in large seeded crops and certain medium and small seeded crops. The method comprises the preemergent application of certain 5-alkylamino-3-oxo-2-optionally substituted phenyl-4-(3-trifluoromethylphenyl)-4,5-dihydrofurans to control weeds in such crops.

17 Claims, No Drawings

PREEMERGENCE WEED CONTROL IN SELECTED CROPS

This application is a continuation of application Ser. No. 947,006, filed on Dec. 29, 1986, now abandoned.

BACKGROUND OF THE INVENTION

This invention relates to weed control in large seeded crops and certain medium and small seeded crops via the application of certain 5-amino-3-oxo-2-phenyl-4-(3-trifluoromethylphenyl)-4,5-dihydrofuran derivatives.

U.S. Pat. No. 4,568,375 discloses a genus of herbicidal compounds having the formula:

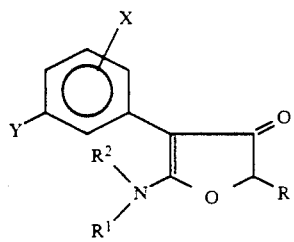

wherein R is alkyl, cycloalkyl, alkenyl, haloalkyl, haloalkenyl, alkoxyalkyl, alkylthioalkyl phenyl, naphth-1-yl, inden-1-yl, substituted aryl or optionally substituted aryl; $R^1$ is hydrogen or alkyl; $R^2$ is hydrogen, alkyl, alkenyl, alkoxycarbonylalkyl, alkoxylalkyl, alkylthioalkyl or $R^1$ and $R^2$ together with the nitrogen atom to which they are joined form a heterocycle; X is hydrogen, alkyl, alkoxyl halo or trifluoromethyl and Y is alkyl, alkoxyl halo, haloalkyl, haloalkoxy or haloalkylthio with certain provisos excluding certain compounds.

This patent teaches that such compounds have both preemergent and postemergent activity and have especially good preemergent activity against a broad spectrum of broadleaf and grassy weeds. The patent further teaches that compounds wherein R is phenyl, methylphenyl, halophenyl, methyl, ethyl, or propyl; and/or one of $R^1$ or $R^2$ is hydrogen and the other is methyl; and/or X is hydrogen and Y is 3-trifluoromethyl are especially preferred. The patent presents Tables of biological data showing high preemergent phytotoxicity for a number of the preferred compounds with respect a variety of weeds and also with respect to soybean and rice.

U.S. Pat. No. 4,596,595 discloses herbicidal compounds having the formula:

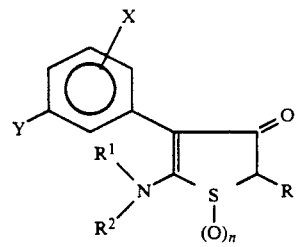

wherein n is 0, 1, or 2; R is alkyl, cycloalkyl, (cycloalkyl)alkylene, alkenyl, haloalkyl, haloalkenyl, alkoxy, alkylthio, alkoxyalkyl, alkylthioalkyl, or certain optionally substituted aryls; $R^1$ is hydrogen or alkyl; $R^2$ is hydrogen, alkyl alkenyl, alkoxycarbonylalkyl, alkoxyalkyl, or alkylthioalkyl; or $R^1$ and $R^2$ together with the nitrogen to which they are joined form a nitrogen heterocycle; X is hydrogen, alkyl, alkoxy, halo, or trifluoromethyl; and Y is alkyl; alkoxy; halo; haloalkyl, haloalkoxy, with provisos excluding certain compounds.

This patent teaches that such compounds exhibit both preemergent and postemergent herbicidal activity and especially good preemergent activity. The patent further teaches that by varying the dosage rate, certain of the compounds exhibit acceptable safety with respect to certain broadleaf crops, notably soybean crops, while retaining a broad spectrum of preemergent herbicidal activity against both broadleaf weeds and grasses.

SUMMARY OF THE INVENTION

It has now been surprisingly discovered that although the dihydrofuran herbicides described in U.S. Pat. No. 4,596,595 exhibit severe preemergent phytotoxicity against a large number of weeds and crops, that certain of the preferred compounds described in U.S. Pat. No. 4,596,595 can be safely applied to provide effective weed control in large seeded crops and certain medium and small seeded crops.

Accordingly, the present invention provides a method for providing preemergent weed control in large seeded crops and certain medium and small seeded crops which comprises applying to the habitat or growth medium of such crops a preemergent herbicidally effective amount which amount is safe with respect to said large seeded crop of a compound having the formula:

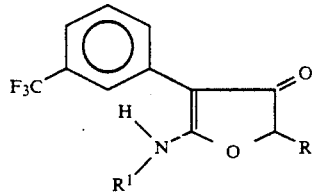

(I)

wherein $R^1$ is methyl or ethyl, R is phenyl, 2-methylphenyl, 2-chlorophenyl, 2-fluorophenyl, or 4-fluorophenyl; and compatible salt thereof.

In a further aspect, the invention provides a method for providing safe early postemergent control of selected weeds in certain crops.

In another aspect the invention provides a herbicidal composition which comprises a preemergent effective amount of the compound of Formula (I) or compatible salts thereof.

The invention will be further described hereinbelow, wherein further aspefcts of the invention which will become apparent.

FURTHER DESCRIPTION OF THE INVENTION AND PREFERRED EMBODIMENTS

It has been found that the compounds of Formula (I) and compatible salts thereof can be safely applied in large seeded crops and certain medium and small seeded crops at rates which are effective to provide preemergent control of a large number of weed species, especially broadleaf weeds. The preferred compounds of Formula (I), in terms of combined crop safety and efficacious weed control are the compounds wherein R is phenyl and $R^1$ is methyl or ethyl, especially methyl.

Typically, the compounds are applied at rates in the range of about from 0.15 to 1.5 lbs/acre, more generally about 0.25 to 1.2 lbs/acre and preferably about from 0.5 to 1 lb/acre. Optimum application rates can vary with the particular crop, soil condition or type of soil, soil texture, etc., the amount of rainfall, and the weed species which need to be controlled.

Generally, it is preferred to use the highest rate which is safe with respect to a given crop and cost effective with respect to weed control.

Examples of large seeded crops to which the present invention can be safely and effectively applied to provide preemergent weed control, include cotton, peanuts, peas sorghum, sunflower, potato and the like. (In the case of potatoes, what is referred to as eyes or seed potatoes are planted rather than seeds in the technical sense.) The compounds of Formula (I) can also be safely and effectively applied in certain medium and small seeded crops such as sorghum, barley and wheat. In the case of crops such as corn, spring wheat and barley, crop safety is strongly influenced by the type of soil and by the particular method in which the herbicide is applied. Thus, with respect to these compounds of Formula (I) crops have shown acceptable safety in high organic matter soils, but relatively poor safety in low organic coarse soils. In the case of corn, it is preferred to use lower application rates.

The compounds show especially good safety and effectiveness in providing preemergent weed control in peanuts, grain sorghum, cotton (non-western), sunflower, peas, potato and lentils. At rates which are safe with respect to the aforementioned crops, the compounds provide effective preemergent weed control of a large number of weeds, including broadleaf weeds, such as, Pitted morninglory (*Ipomoea lacunosa*);
Smallflower morningglory (*Jacquemontia tamnifolia*);
Entire leaf morningglory (*Ipomoea hederacea*);
Ivyleaf morningglory (*Ipomoea hederacea*);
Tall morningglory (*Ipomoea purpurea*);
Palmleaf morningglory (*Ipomoea wrightii*);
Redroot pigweed (*Amaranthus retroflexus*);
Smooth pigweed (*Amaranthus hybridus*);
Spiny amaranth (*Amaranthus spinosus*);
Palmer amaranth (*Amaranthus palmeri*);
Prickly sida (*Sida spinosa*);
Velvetleaf (*Abutilon theophrasti*);
Spurred anoda (*Anoda cristata* );
Sicklepod (*Cassia obtusifolia*);
Hemp sesbania (*Sesbania exaltata*);
Common purslane (*Portulaca oleracea*);
Carpetweed (*Mollugo verticillata*);
Florida purslant (*Richardia scabra*);
Common lambsquarters (*Chenopodium album*);
Annual smartweeds (Polygonum spp.);
Florida beggarweed (*Desmodium tortuosum*);
Common ragweed (*Ambrosia artemisifolia*);
Coffee senna (*Cassia occidentalis*);
Redweed (*Melochia corchorifolia*);
Black night shade (*Solanum nigrum*);
Jimsonweed (*Datura stramonium*);
Kochia (*Kochia scoparia*);
Wild radish (*Raphanus raphanistrum*) and grasses and sedges, such as
Giant foxtail (*Setaria faberi*);
Green foxtail (*Seteria viridis*);
Yellow foxtail (*Setaria glauca*);
Barnyardgrass (*Echinochloa crus-galli*);
Jungle rice (*Echinochloa colonum*);
Large crabgrass (*Digitaria sanguinalis*);
Smooth crabgrass (*Digitaria ischaemum*);
Fall panicum (*Panicum dichotomiflorum*);
Annual sedges (Cyperus spp.) and the like.

The compounds provide especially good preemergent control of problem weeds, such as sicklepod, morning glories, and Florida beggarweed. The compounds also suppress certain broadleaf weeds, such as spotted spurge (*Euphorbia maculata*); common cocklebur (*Xanthium strumarium*); wild mustard and grasses and sedges, such as Broadleaf signalgrass (*Brachiaria platyphylla*);
Goosegrass (*Eleusine indica*);
Yellow nutsedge (*Cyperus esculentus*);
Purple nutsedge (*Cyperus rotundus*);
Sprangletops (*Leptochloa spp.*);
Crowfootgrass (*Dactyloctenium aegyptium*); and
Texas panicum (*Panicum texanum*);
Seedling Johnsongrass (*Sorghum halepense*); at safe preemergent rates, even though they do not provide complete preemergent weed control at these rates. (Generally, a weed is considered suppressed when its growth is reduced to the point that it cannot effectively compete with the crop).

The preemergence herbicidal effect can be achieved with respect to said weeds by applying the present herbicide either before or up to one or two days after the weed(s) crack the soil. The present herbicide also exhibits some postemergent effect but, generally, this is substantially less and limited to certain weed species. The present herbicide is especially useful to control certain significant weed problems in peanuts, as will be subsequently explained.

Typically, for preemergence weed control, the compounds of Formula (I) are applied about from 7 days before planting of the crop to about 3 days after planting. More preferably, the compounds are applied about from 2 days before planting to about 1 or 2 days after planting. Optimum application times can vary with the particular crop, soil condition and predominant weed species to be controlled. The compounds can be applied by simple layering over the soil or more preferably, under dry or normal moisture conditions, can be mixed into the soil prior to planting. It has been found that weed control is generally enhanced under dry or normal soil conditions, by dividing the herbicide into two portions and mixing one portion of the herbicide into the soil at the time of planting and then applying the other portion to the top of the soil shortly before or preferably shortly after planting. Generally, the compounds of Formula (I) or salts are typically applied as compositions or formulations comprising effective amounts of the compounds and an acceptable carrier.

An acceptable or compatible carrier (agriculturally acceptable carrier) is one which does not significantly adversely affect the desired biological effect achieved by the active compound, save to dilute it. Typically, the composition contains about from 0.01 to 1.2 wt. %, preferably 0.1 to 0.8 wt. % of the compound(s) of Formula (I) or mixtures thereof. Concentrates can also be made having high concentrations designed for dilution prior to application. The carrier can be a solid, liquid, or aerosol. The actual compositions can take the form of granules, powders, dusts, solutions, emulsions, slurries, aerosols, and the like. Typically, the composition is prepared as an emulsion or wettable powder concentrate which is then mixed with the appropriate amount of water to give the desired concentration just prior to application.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, diumethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters, surface-active agents, and/or agents which affect the leachability of the compound or otherwise enhance soil stability. The composition can also contain various compatible adjuvants, stabilizers, conditioners, insecticides, fungicides, and if desired, other compatible herbicidally active compounds. It is preferred to apply surface applications after planting up to the time the crop emerges through or breaks the soil. Desirably, sufficient moisture should be provided to move the herbicide into the soil.

Examples of preferred concentrate compositions include:

A preferred example of an emulsion concentrate is one containing about 18-19 wt. % of the compound(s) of Formula I, 60-62 wt. % isophorone; about 10 wt. % of an anionic and nonionic surfactant mixture, for example, that sold under the trademark Polyfac 804 by Westvaco of Charleston Heights, S.C., U.S.A.; and about 10 wt. % of a nonionic and anionic surfactant blend such as sold under the trademark Atlox 3455F by ICI Americas of Wilmington, Del., U.S.A.

A preferred wettable powder concentrate, for example, contains about 50-80 wt. % of the compound(s) of Formula I; about 1-2 wt. % of a suspension agent, for example, a sodium salt of condensed naphthylate sulphonic acid; about 10-40 wt. % kaolin clay; about 3-5 wt. % of a sodium salt of lignin sulfonate; about 1 wt. % mixed sulfonated alkyl carboxylate and sulfonated alkyl naphthylated sodium salts; and about 3-5 wt. % of a sodium salt of naphthylene-formaldehyde condensate.

It has been found that the compounds of Formula I can be used to effect safe early stage postemergence control of beggarweed, Jimsonweed, Velvetleaf, and sicklepod in peanuts. Typically, the compounds are applied at a rate of about from 0.15 to 1.5 lbs/acre, preferably about 0.5 to 1.0 lb/acre. In order to provide efficacious control of these weeds, the weeds should be treated with the compounds before they have reached a height of 6 inches and most preferably, before the weeds have reached 3 inches in height. Best results are generally obtained by treating the weeds before they are about 2 inches. The compounds are typically applied by simply contacting the foliage of the weeds with the compounds or more appropriately, as a composition containing the compounds of Formula I and a compatible carrier, such as described above. The addition of a surfactant improves postemergence phytotoxicity with respect to said weeds, while retaining safety with respect to peanuts. Typically, where a surfactant is used, typically the spray contains about 0.3 to 3% by volume, preferably about 0.5 to 2% by volume of the surfactant.

The compounds of Formula (I) and their salts are known compounds and can be prepared by the procedures described in U.S. Pat. No. 4,568,376 which procedures are hereby incorporated by reference in their entirety.

Definitions

As used herein, the following terms have the following meanings unless expressly stated to the contrary:

The term "compatible salts" refers to salts of the present compound which do not significantly adversely affect the herbicidal properties of the parent compound. Suitable salts include cation salts, such as, for example, the cation salts of lithium, sodium, potassium, alkali earth metals, ammonia, quaternary ammonium salts; acid addition salts, for example, hydrochloride, hydrobromide, hydrofluoride, hydrosulfate salts and the like.

The term "compounds of Formula I" or like expressions as used generally in the present description, refers to the compounds of Formula I and compatible salts thereof.

The terms "safe" or "safety" as applied with respect to a crop(s) and given herbicide, refers to a herbicide which does not produce any injury with respect to that crop(s) or only causes an amount of injury which the crop(s) can grow out of without substantial loss in yield. Correspondingly, the term "safe amount" refers to an amount of a given herbicide which does not produce any injury with respect to a given crop(s) or only causes an amount of injury which the crop(s) can grow out of without substantial loss in yield.

The term "control" as applied to weed(s), refers to destruction of said weeds. An amount of a herbicidal effect to control weeds refers to an amount which is effective to destroy or suppress at least a major portion of a given weed specie(s).

The term "suppress" as applied to weeds, refers to a condition where the growth of the weed is reduced to the point that it cannot effectively compete with the crop.

A further understanding of the invention can be had from the following non-limiting examples.

EXAMPLES

Example 1

In this example, the compounds identified in Table A were field-tested for both preemergent herbicidal activity and crop safety with respect to a variety of weeds and crops. The tests were conducted in late August through September in Greenville, Mississippi (Dundee very fine sandy loam). Plots 6 ft×25 ft were replicated four times in a randomized complete block design. Preplant incorporated and surface treatments were made on the same day as planting. Preplant incorporated treatments are made by tilling the test compound into the soil prior to planting. Surface treatments are made after planting. Weed seeds and crop seeds were planted at the appropriate depth (drilled) in 20" rows. The crops and weeds were evaluated visually 23 days and 30 days after planted. Complete destruction (phytotoxicity) of the weed or crop is assigned a value of 100%. Complete absence of phytotoxicity or crop injury is assigned a value of 0. Each test compound was evaluated at three rates (i.e., 0.25 lbs/acre; 0.5 lbs/acre and 1.0 lbs/acre). The compounds were applied as an aqueous emulsion containing the test compound, a non-phytotoxic organic solvent (e.g., cyclohexanone) and a small amount of a non-phytotoxic emulsifying agent.

The results of this testing, expressed as an average of the replicates for each testing, are set forth in Tables 1 and 2 hereinbelow.

TABLE A

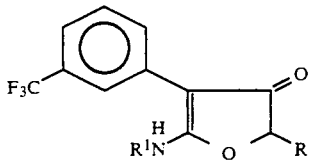

TABLE B

| Abbreviation | Weed |
|---|---|
| Mo. | Morningglory |
| Pr.S | Prickly Sida |
| Cof. | Coffeeweed |
| Sp. a. | Spurred anoda |
| Ve. | Velvetleaf |
| Si P. | Sicklepod |
| Jg | Johnsongrass |
| Gg | Goosegrass |
| Pw | Pigweed |
| Up.S. | Upright Spurge |
| Pu.Nut | Purple Nutsedge |

TABLE 1

Preemergent Crops Phytotoxicity

| Compound No. | Application Rate (lbs/acre) and Method | Evaluation Days After Treatment | Percent Phytotoxicity ||||||
|---|---|---|---|---|---|---|---|---|
| | | | Peanuts | Cotton | Soybean | Corn | Cowpeas | Sorghum |
| 1 | 0.25-S | 23 | 5 | 0 | 38 | 15 | 0 | 0 |
| 1 | 0.5-S | 23 | 5 | 10 | 63 | 30 | 0 | 10 |
| 1 | 1.0-S | 23 | 0 | 18 | 68 | 50 | 47 | 20 |
| 1 | 0.25-S | 30 | 0 | 0 | 40 | 30 | 3 | 3 |
| 1 | 0.5-S | 30 | 0 | 23 | 70 | 28 | 13 | 20 |
| 1 | 1.0-S | 30 | 0 | 15 | 70 | 53 | 47 | 33 |
| 2 | 0.25-S | 23 | 0 | 0 | 33 | 23 | 0 | 0 |
| 2 | 0.5-S | 23 | 10 | 0 | 50 | 28 | 20 | 23 |
| 2 | 1.0-S | 23 | 8 | 18 | 58 | 50 | 0 | 13 |
| 2 | 0.25-S | 30 | 0 | 8 | 38 | 18 | 0 | 5 |
| 2 | 0.5-S | 30 | 8 | 18 | 50 | 35 | 7 | 20 |
| 2 | 1.0-S | 30 | 0 | 20 | 50 | 45 | 7 | 25 |
| 3 | 0.25-S | 23 | 15 | 8 | 55 | 25 | 0 | 30 |
| 3 | 0.5-S | 23 | 17 | 33 | 53 | 0 | 0 | 13 |
| 3 | 1.0-S | 23 | 10 | 23 | 68 | 33 | 10 | 18 |
| 3 | 0.25-S | 30 | 0 | 10 | 50 | 20 | 10 | 30 |
| 3 | 0.5-S | 30 | 0 | 23 | 37 | 20 | 10 | 27 |
| 3 | 1.0 | 30 | 0 | 25 | 50 | 30 | 10 | 23 |
| 4 | 0.25-S | 23 | 5 | 0 | 33 | 65 | 47 | 55 |
| 4 | 0.5-S | 23 | 10 | 0 | 73 | 90 | 73 | 93 |
| 4 | 1.0-S | 23 | 0 | 43 | 98 | 100 | 90 | 100 |
| 4 | 0.25-S | 30 | 0 | 5 | 38 | 68 | 43 | 50 |
| 4 | 0.5-S | 30 | 3 | 18 | 75 | 95 | 73 | 93 |
| 4 | 1.0-S | 30 | 5 | 30 | 98 | 100 | 90 | 96 |
| 1 + 1** | .25P + .25S | 23 | 5 | 13 | 100 | 93 | 38 | 35 |
| 1 + 1** | .5P + .5S | 23 | 8 | 80 | 100 | 100 | 100 | 65 |
| 1 + 1** | .25P + .25S | 30 | 0 | 15 | 100 | 95 | 25 | 33 |
| 1 + 1** | .5P + .5S | 30 | 0 | 80 | 100 | 100 | 100 | 65 |
| 2 + 2** | .25P + .25S | 23 | 0 | 10 | 70 | 53 | 5 | 18 |
| 2 + 2** | .5p + .5S | 23 | 13 | 10 | 88 | 100 | 5 | 58 |
| 2 + 2** | .25P + .25S | 30 | 3 | 20 | 73 | 73 | 10 | 25 |
| 2 + 2** | .5P + .5S | 30 | 0 | 13 | 90 | 98 | 18 | 63 |

*S = Surface spray after planting
*P = Mixed (tilled) into soil prior to planting
**Compound divided into two equal portions, one portion mixed into soil prior to planting and the other portion applied to the surface of the soil after planting. Both applications and planting were made on the same day.

| Compound No. | R | $R^1$ |
|---|---|---|
| 1 | phenyl | methyl |
| 2 | phenyl | ethyl |
| 3 | 2-fluorophenyl | ethyl |
| 4 | methyl | methyl |

TABLE 2

Preemergent Phytotoxicity

| Compound No. | Application Rate (lbs/acre) and Method | Evaluation Days After Treatment | Weeds* Percent Control |||||||||||
|---|---|---|---|---|---|---|---|---|---|---|---|---|---|
| | | | Mo. | Pr.S. | Cof. | Sp.a. | Ve. | Si.P. | Jg | Gg | Pw | Up.S. | Pu.Nut |
| 1 | 0.25-S* | 23 | 80 | 94 | 78 | 100 | 100 | 98 | 53 | 10 | 98 | 25 | 35 |
| 1 | 0.5-S | 23 | 95 | 100 | 95 | 100 | 100 | 100 | 83 | 23 | 100 | 80 | 35 |
| 1 | 1.0-S | 23 | 100 | 100 | 100 | 100 | 100 | 100 | 100 | 90 | 100 | 100 | 38 |
| 1 | 0.25-S | 30 | 78 | 85 | 75 | 100 | 100 | 93 | 20 | 0 | 93 | 18 | 20 |

TABLE 2-continued

Preemergent Phytotoxicity

| Compound No. | Application Rate (lbs/acre) and Method | Evaluation Days After Treatment | Weeds* Percent Control | | | | | | | | | | |
|---|---|---|---|---|---|---|---|---|---|---|---|---|---|
| | | | Mo. | Pr.S. | Cof. | Sp.a. | Ve. | Si.P. | Jg | Gg | Pw | Up.S. | Pu.Nut |
| 1 | 0.5-S | 30 | 93 | 100 | 98 | 100 | 100 | 100 | 68 | 13 | 98 | 75 | 40 |
| 1 | 1.0-S | 30 | 99 | 100 | 98 | 100 | 100 | 100 | 98 | 55 | 100 | 93 | 23 |
| 2 | 0.25-S | 23 | 60 | 90 | 50 | 99 | 93 | 90 | 75 | 0 | 97 | 63 | 13 |
| 2 | 0.5-S | 23 | 90 | 98 | 83 | 100 | 100 | 98 | 95 | 93 | 100 | 88 | 35 |
| 2 | 1.0-S | 23 | 85 | 96 | 91 | 98 | 100 | 98 | 93 | 65 | 100 | 99 | 35 |
| 2 | 0.25-S | 30 | 58 | 73 | 25 | 100 | 93 | 95 | 53 | 15 | 90 | 58 | 35 |
| 2 | 0.5-S | 30 | 85 | 93 | 78 | 100 | 100 | 100 | 85 | 78 | 100 | 93 | 35 |
| 2 | 1.0-S | 30 | 85 | 95 | 95 | 100 | 100 | 100 | 90 | 86 | 98 | 93 | 30 |
| 3 | 0.25-S | 23 | 48 | 94 | 44 | 98 | 88 | 65 | 85 | 35 | 100 | 48 | 30 |
| 3 | 0.5-S | 23 | 90 | 97 | 87 | 100 | 100 | 100 | 100 | 97 | 100 | 93 | 43 |
| 3 | 1.0-S | 23 | 91 | 99 | 93 | 100 | 100 | 99 | 100 | 89 | 100 | 88 | 50 |
| 3 | 0.25-S | 30 | 48 | 95 | 50 | 93 | 83 | 68 | 80 | 33 | 98 | 33 | 25 |
| 3 | 0.5-S | 30 | 80 | 97 | 80 | 100 | 100 | 100 | 97 | 93 | 100 | 85 | 30 |
| 3 | 1.0-S | 30 | 85 | 100 | 85 | 100 | 100 | 100 | 100 | 88 | 100 | 83 | 35 |
| 4 | 0.25-S | 23 | 20 | 60 | 8 | 18 | 20 | 35 | 83 | 63 | 5 | 50 | 25 |
| 4 | 0.5-S | 23 | 65 | 85 | 10 | 60 | 65 | 65 | 100 | 100 | 15 | 63 | 28 |
| 4 | 1.0-S | 23 | 86 | 98 | 75 | 95 | 98 | 100 | 100 | 100 | 50 | 98 | 35 |
| 4 | 0.25-S | 30 | 5 | 40 | 0 | 25 | 18 | 35 | 58 | 70 | 10 | 50 | 25 |
| 4 | 0.5-S | 30 | 63 | 88 | 8 | 48 | 48 | 65 | 93 | 100 | 15 | 68 | 23 |
| 4 | 1.0-S | 30 | 85 | 95 | 68 | 95 | 100 | 100 | 100 | 100 | 38 | 93 | 28 |
| 1 + 1** | .25P + .25S | 23 | 100 | 100 | 98 | 100 | 100 | 98 | 98 | 20 | 100 | 53 | 53 |
| 1 + 1** | .5P + .5S | 30 | 100 | 100 | 100 | 100 | 100 | 98 | 100 | 74 | 100 | 89 | 80 |
| 1 + 1** | .25P + .25S | 30 | 100 | 100 | 100 | 100 | 100 | 100 | 96 | 5 | 100 | 38 | 30 |
| 1 + 1** | .5P + .5S | 23 | 100 | 100 | 100 | 100 | 100 | 100 | 98 | 40 | 100 | 90 | 63 |
| 2 + 2** | .25P + .25S | 23 | 63 | 100 | 90 | 100 | 100 | 93 | 90 | 38 | 100 | 63 | 30 |
| 2 + 2** | .5p + .5S | 30 | 95 | 100 | 98 | 100 | 100 | 100 | 100 | 90 | 100 | 95 | 45 |
| 2 + 2** | .25P + .25S | 30 | 63 | 100 | 88 | 100 | 100 | 93 | 90 | 20 | 100 | 58 | 18 |
| 2 + 2** | .5P + .5S | 30 | 90 | 100 | 100 | 100 | 100 | 100 | 100 | 93 | 100 | 91 | 48 |

*S = Surface spray after planting
*P = Mixed (tilled) into soil prior to planting
**Compound divided into two equal portions, one portion mixed into soil prior to planting and the other portion applied to the surface of the soil after planting. Both applications and planting were made on the same day.

As can be seen from the above tables, Compounds Nos. 1 and 2 afforded the best combination of weed control and crop safety. Both compounds were safe with respect to cotton at all three surface application rates. In the case of Compound No. 2, 23% phytotoxicity, is about the threshold of acceptable phytotoxicity with respect to cotton, which is generally considered to tolerate up to 20% phytotoxicity. Moreover, since phytotoxicity was only 15% at 1-lb/acre, it is probable that the 23% phytotoxicity at 0.5-lb/acre was unduly high. At 1-lb/acre both compounds afforded excellent weed control of 9 of the 11 weed species tested and moderate control of an eleventh (Goosegrass). Both compounds were also safe with respect to cowpeas and sorghum at surface application rates of 0.25 and 0.5 lb/acre and marginally safe with respect to corn at 0.25 lb/acre. At a surface application rate, 0.5 lb/acre Compound No. 1 afforded acceptable or excellent preemergent weed control with respect to 9 of the 12 weed species tested. At this rate, Compound No. 2 afforded acceptable or excellent weed control with respect to 10 of the 11 weed species tested. At 0.25 lbs/acre surface application, Compound No. 1 still provided acceptable or excellent weed control with respect to 7 of the weeds tested and Compound No. 2 provided acceptable or excellent weed control with respect to six of the weed species tested. At the rates tested none of the compounds provided acceptable weed control with respect to purple nutsedge when applied as pure surface applications. When Compounds 1 and 2 were applied, both preplant incorporated (i.e., mixed into the soil prior to planting), and as a surface application following planting, phytotoxicity increased. Thus, increasing weed control efficiency and reducing safety. At the rates tested, none of the compounds tested was safe with respect to soybean.

Example 1A

In this Example, the compounds identified in Table A were field-tested for postemergence phytotoxicity with respect to the same crops and weed species as used in Example 1. These tests were conducted in Greenville, Miss. at about the same time as the preemergent tests using the same general testing design as described in Example 1.

The postemergence tests were conducted by spraying the crops and weeds with an aqueous solution of the test compound containing 0.25 % by vol. of a nonionic surfactant, two weeks after planting using the dosage rates indicated in Tables 3 and 4 hereinbelow. The approximate growth stage of the crops and weeds at the time of planting is given in Table C hereinbelow. The plants were visually evaluated for percent phytotoxicity nine days and sixteen days after spraying. Complete destruction of the plants is assigned a value of 100. The absence of any observable injury is assigned a value of 0. The results of this test expressed as the average of the replicates for a given compound and application rate are given in Tables 3 and 4 hereinbelow.

TABLE C

| Growth Stage of Plants at Time of Postemergent Spraying | | |
|---|---|---|
| Peanuts | 4 to 5 leaves | 3 to 4 inches tall |
| Cotton | 3 true leaves | 5 inches tall |
| Soybeans | 4 to 5 leaves | 2 to 4 inches tall |
| Cowpeas | 3 to 4 leaves | 3 to 6 inches tall |
| Corn | 3 to 4 leaves | 7 to 10 inches tall |
| Sorghum | 3 to 4 leaves | 8 to 10 inches tall |
| Johnsongrass | 4 leaves | 4 to 6 inches tall |
| Goosegrass | 4 leaves | ½ to 1 inch tall |

TABLE C-continued

Growth Stage of Plants at Time of Postemergent Spraying

| | | |
|---|---|---|
| Morningglory | 4 to 5 leaves | 3 to 4 inches tall |
| Prickly sida | 2 to 3 leaves | ½ to 1 inch tall |
| Coffeeweed | 3 to 4 leaves | 3 to 4 inches tall |
| Spurred anoda | 4 to 5 leaves | 2 to 3 inches tall |
| Velvetleaf | 3 leaves | 3 to 4 inches tall |
| Sicklepod | 2 to 3 leaves | 2 to 3 inches tall |
| Pigweed | 6 to 7 leaves | 1 to 5 inches tall |
| Purple Nutsedge | 1 to 4 leaves | 1 to 4 inches tall | the weed tested Compounds Nos. 1 and 2 provided commercially acceptable weed control only with respect to pigweed and upright spurge.

Example 2

In this example, 5-methylamino-3-oxo-4-(3-trifluoromethylphenyl)-2,3-dihydrofuran (Compound 1) was tested for preemergent herbicidal activity and crop safety. This testing was conducted in the greenhouse under a controlled environment using clay loam soil.

Seeds of the test vegetation were planted in a pot of

TABLE 3

Postemergent Phytotoxicity

| Compound No. | Application Rate (lbs/acre) and Method | Evaluation Days After Treatment | Crops Percent Phytotoxicity | | | | | |
|---|---|---|---|---|---|---|---|---|
| | | | Peanut | Cotton | Soybean | Corn | Cowpeas | Sorghum |
| 1 | 0.25* | 9 | 0 | 23 | 55 | 30 | 53 | 5 |
| 1 | 0.5 | 9 | 0 | 25 | 50 | 30 | 60 | 10 |
| 1 | 1.0 | 9 | 10 | 25 | 53 | 23 | 53 | 20 |
| 1 | 0.25 | 16 | 3 | 40 | 43 | 30 | 23 | 20 |
| 1 | 0.5 | 16 | 0 | 53 | 48 | 30 | 50 | 20 |
| 1 | 1.0 | 16 | 10 | 60 | 65 | 40 | 53 | 33 |
| 2 | 0.25 | 9 | 8 | 23 | 53 | 25 | 13 | 0 |
| 2 | 0.5 | 9 | 0 | 30 | 45 | 20 | 37 | 0 |
| 2 | 1.0 | 9 | 15 | 23 | 53 | 28 | 60 | 0 |
| 2 | 0.25 | 16 | 3 | 40 | 38 | 23 | 23 | 20 |
| 2 | 0.5 | 16 | 3 | 45 | 43 | 30 | 30 | 23 |
| 2 | 1.0 | 16 | 0 | 48 | 45 | 28 | 43 | 25 |
| 3 | 0.25 | 9 | 10 | 28 | 53 | 5 | 7 | 0 |
| 3 | 0.5 | 9 | 10 | 25 | 50 | 15 | 7 | 5 |
| 3 | 1.0 | 9 | 15 | 33 | 55 | 18 | 17 | 20 |
| 3 | 0.25 | 16 | 3 | 40 | 38 | 28 | 13 | 20 |
| 3 | 0.5 | 16 | 0 | 53 | 40 | 20 | 20 | 18 |
| 3 | 1.0 | 16 | 3 | 65 | 63 | 35 | 30 | 30 |
| 4 | 0.25 | 9 | 0 | 10 | 55 | 10 | 30 | 0 |
| 4 | 0.5 | 9 | 15 | 23 | 45 | 25 | 27 | 0 |
| 4 | 1.0 | 9 | 0 | 10 | 40 | 8 | 33 | 0 |
| 4 | 0.25 | 16 | 20 | 35 | 30 | 15 | 17 | 13 |
| 4 | 0.5 | 16 | 17 | 33 | 33 | 13 | 27 | 8 |
| 4 | 1.0 | 16 | 17 | 30 | 35 | 28 | 30 | 20 |

TABLE 4

Postemergent Phytotoxicity

| Compound No. | Application Rate (lbs/acre) and Method | Evaluation Days After Treatment | Weeds* Percent Control | | | | | | | | | |
|---|---|---|---|---|---|---|---|---|---|---|---|---|
| | | | Mo. | Pr.S. | Cof. | Sp.a. | Ve. | Si.P. | Jg | Gg | Pw | Up.S. | P.Nut |
| 1 | 0.25* | 9 | 38 | 38 | 35 | 38 | 43 | 48 | 0 | 0 | 45 | 33 | 15 |
| 1 | 0.5 | 9 | 50 | 55 | 53 | 53 | 55 | 70 | 0 | 10 | 65 | 67 | 20 |
| 1 | 1.0 | 9 | 65 | 65 | 53 | 70 | 58 | 68 | 5 | 13 | 83 | 93 | 20 |
| 1 | 0.25 | 16 | 33 | 8 | 25 | 20 | 40 | 28 | 5 | 0 | 50 | 17 | 7 |
| 1 | 0.5 | 16 | 45 | 30 | 50 | 50 | 68 | 78 | 0 | 0 | 70 | 68 | 20 |
| 1 | 1.0 | 16 | 65 | 65 | 63 | 70 | 73 | 78 | 13 | 0 | 85 | 80 | 13 |
| 2 | 0.25 | 9 | 30 | 30 | 38 | 48 | 55 | 50 | 8 | 15 | 45 | 63 | 38 |
| 2 | 0.5 | 9 | 45 | 58 | 43 | 63 | 58 | 58 | 0 | 13 | 68 | 70 | — |
| 2 | 1.0 | 9 | 48 | 70 | 40 | 65 | 60 | 60 | 8 | 18 | 68 | 67 | 60 |
| 2 | 0.25 | 16 | 28 | 0 | 35 | 48 | 68 | 53 | 0 | 0 | 53 | 68 | 8 |
| 2 | 0.5 | 16 | 40 | 35 | 40 | 65 | 80 | 50 | 5 | 0 | 78 | 90 | — |
| 2 | 1.0 | 16 | 40 | 55 | 30 | 65 | 73 | 60 | 8 | 0 | 80 | 75 | 3 |
| 3 | 0.25 | 9 | 33 | 63 | 50 | 58 | 58 | 60 | 0 | 8 | 68 | 87 | 50 |
| 3 | 0.5 | 9 | 40 | 48 | 45 | 65 | 65 | 58 | 0 | 12 | 78 | 73 | 30 |
| 3 | 1.0 | 9 | 50 | 53 | 53 | 68 | 63 | 68 | 8 | 23 | 85 | 90 | 50 |
| 3 | 0.25 | 16 | 23 | 35 | 40 | 50 | 73 | 60 | 0 | 0 | 58 | 93 | 10 |
| 3 | 0.5 | 16 | 28 | 20 | 38 | 60 | 70 | 45 | 0 | 8 | 73 | 50 | 0 |
| 3 | 1.0 | 16 | 45 | 50 | 53 | 76 | 73 | 70 | 0 | 5 | 98 | 93 | 25 |
| 4 | 0.25 | 9 | 25 | 30 | 23 | 30 | 40 | 40 | 0 | 13 | 33 | 13 | 30 |
| 4 | 0.5 | 9 | 30 | 38 | 25 | 40 | 35 | 48 | 0 | 40 | 48 | 57 | 30 |
| 4 | 1.0 | 9 | 33 | 30 | 30 | 40 | 40 | 45 | 0 | 38 | 40 | 60 | 40 |
| 4 | 0.25 | 16 | 8 | 8 | 10 | 20 | 15 | 8 | 0 | 0 | 25 | 10 | 7 |
| 4 | 0.5 | 16 | 13 | 0 | 13 | 20 | 38 | 23 | 0 | 13 | 35 | 43 | 10 |
| 4 | 1.0 | 16 | 8 | 0 | 18 | 20 | 33 | 13 | 5 | 30 | 30 | 10 | 23 |

As can be seen from Tables 3 and 4, Compounds Nos. 1 and 2 were only safe with respect to peanut of the crops tested, when applied postemergence. Further, of soil. An aqueous solution of the test compound containing a small amount of surfactant and acetone were sprayed uniformly onto the soil surface at the application rate given in Table 5 hereinbelow. The pot was watered and placed in a greenhouse. The pot was watered intermittently and observed for seedling emergence, health of emerging seedlings, etc., for a 3-week period. At the end of this period, the herbicidal effectiveness of the compound was rated based on the symptoms of physiological response. A 0-to-100 scale was used, 0 representing no phytotoxicity, 100 representing complete kill. Three replicates were used for each application rates. The results are reported as an average of the replicates for that dosage rate. These results are summarized in Table 5 hereinbelow.

TABLE 5

Preemergent Phytotoxicity in Clay Loam

| | Rate Microgram/cm² | | | |
|---|---|---|---|---|
| | 1.8 | .72 | .29 | .12 |
| | % Phytotoxicity | | | |
| BROADLEAF CROPS | | | | |
| Peanuts | 0 | 0 | 0 | 0 |
| Soybean | 50 | 8 | 0 | 0 |
| Cotton | 0 | 0 | 0 | 0 |
| BROADLEAF WEEDS | | | | |
| Velvetleaf | 100 | 86 | 0 | 0 |
| Spurred Anoda | 100 | 100 | 83 | 0 |
| Jimson Weed | 100 | 96 | 0 | 0 |
| An. Morningglory | 53 | 36 | 26 | 0 |
| Prickly Sida | 100 | 100 | 70 | 50 |
| Comm. Cocklebur | 0 | 0 | 0 | 0 |
| GRASS WEEDS AND NUTSEDGE | | | | |
| Signalgrass | 0 | 0 | 0 | 0 |
| Yellow Nutsedge | 60 | 20 | 0 | 0 |
| Goosegrass | 13 | 0 | 0 | 0 |
| Yellow Foxtail | 97 | 70 | 20 | 0 |
| Johnsongrass | 50 | 0 | 0 | 0 |

One microgram per square cm. = 0.089 lbs/acre.

Example 3

In this example, a greenhouse preemergent test was conducted on Compound No. 1, in sandy clay loam soil. The same general procedure as described in Example 2 was used with the exception that the number of weed species and crops was expanded and the application rates indicated in Table 6 hereinbelow were used. The results of this testing are shown in Table 6 hereinbelow.

TABLE 6

Preemergent Phytotoxicity in Sandy Clay Loam

| | Rate Microgram/cm² | | | |
|---|---|---|---|---|
| | 1.8 | .72 | .29 | .12 |
| | % Phytotoxicity | | | |
| BROADLEAF CROPS | | | | |
| Sugar Beets | 100 | 100 | 100 | 50 |
| Soybean | 92 | 60 | 20 | 0 |
| Cotton | 12 | 0 | 0 | 0 |
| GRASS CROPS | | | | |
| Barley | 25 | 0 | 0 | 0 |
| Rice (MS) | 87 | 75 | 15 | 0 |

TABLE 6-continued

Preemergent Phytotoxicity in Sandy Clay Loam

| | Rate Microgram/cm² | | | |
|---|---|---|---|---|
| | 1.8 | .72 | .29 | .12 |
| | % Phytotoxicity | | | |
| Sorghum (NK125) | 47 | 15 | 0 | 0 |
| Anza Wheat | 70 | 40 | 0 | 0 |
| Field Corn | 62 | 55 | 35 | 0 |
| BROADLEAF WEEDS | | | | |
| Velvetleaf | 100 | 100 | 89 | 30 |
| Redroot Pigweed | 100 | 100 | 100 | 90 |
| Wild Mustard | 100 | 100 | 100 | 80 |
| Sicklepod | 98 | 100 | 15 | 0 |
| An. MorningGlory | 92 | 32 | 0 | 0 |
| Kochia | 100 | 92 | 92 | 20 |
| Prickly Sida | 100 | 100 | 96 | 87 |
| Comm. Cocklebur | 75 | 0 | 0 | — |
| GRASS WEEDS AND NUTSEDGE | | | | |
| Blackgrass | 99 | 90 | 80 | 35 |
| Wild Oats | 95 | 90 | 60 | 17 |
| Cheatgrass | 27 | 0 | 0 | 0 |
| Yellow Nutsedge | 95 | 75 | 7 | 0 |
| Crabgrass | 100 | 100 | 90 | 40 |
| CA Barnyardgrass | 100 | 85 | 27 | 10 |
| Fall Panicum | 97 | 82 | 30 | — |
| Yellow Foxtail | 97 | 47 | 5 | 0 |
| Johnsongrass | 98 | 89 | 52 | 15 |

Example 4

This example illustrates early postemergent control of beggarweed and sicklepod in peanuts.

In this example, Compound No. 1 was field-tested for safety and efficacy for postemergence control of beggarweed in sicklepod in peanuts. These tests were conducted in during the summer and fall (ending late October) in Florida. A 50% Compound No. 1 wettable powder formulations was mixed with the appropriate amount of water and sprayed at the application rate indicated in Table 7 hereinbelow. The tests were conducted using weeds of different maturity (size). The size of the weeds are reported in Table 7. The results of these tests are reported in Table 7 as an average of the tests conducted for that application rate and weed size. Phytotoxicity was evaluated and recorded in the same manner as described in Example 1. Wherein a value of 0 indicates no effect and a value of 100 indicates complete destruction of the plant. The plants were evaluated 16 days after spraying.

TABLE 7

| | Weed Height | Beggarweed | | | Sicklepod | | | Peanuts |
|---|---|---|---|---|---|---|---|---|
| Dosage lbs/acre | Inches | ¾ | 3 | 11 | 1 | 3 | 9 | 6 |
| | No. of Leaves | 0 | 4 | 9 | 0 | 3 | 7 | 33 |
| 0.75 | | 100 | 96 | 3 | 100 | 80 | 8 | 0 |
| 0.50 | | 100 | 85 | 0 | 96 | 35 | 2 | 0 |
| 0.375 | | 100 | 68 | 0 | 99 | 8 | 0 | 0 |
| 0.25 | | 99 | 28 | 0 | 94 | 13 | 0 | 0 |

As can be seen from the above table, Compound No. 1 provided excellent control of seedling or small beggarweed and sicklepod at all the dosage rates. The compound also provided acceptable control of 3-inch beggarweed at the 0.50 and 0.75 lb/acre rates and acceptable control of 3-inch sicklepod at 0.75 lb/acre. The compound was safe with respect to peanuts at this rate.

Example 4A

In this example Compound No. 1 was field-tested in Florida with respect to beggarweed, sicklepod and peanuts at 0.25 lb/acre in the same manner as described in Example 4, but in this case the spray contained 1% by volume of a surfactant sold under the trademark XE-77 by the Ortho Division of Chevron Chemical Company, a corporation of Delaware, U.S.A. The tests are evaluated 16 days after spraying.

The results of this testing are reported as an average of the weeds tested and are reported in Table 8 hereinbelow wherein 0 indicates no effect and 100 indicates complete destruction.

TABLE 8

| Dosage lbs/acre | Weed Height | Beggarweed | | | Sicklepod | | | Peanuts |
|---|---|---|---|---|---|---|---|---|
| | Inches | ⅜ | 3 | 11 | 1 | 3 | 9 | 6 |
| | No. of Leaves | 0 | 4 | 9 | 0 | 3 | 7 | 33 |
| .25 | | 99 | 91 | 2 | 96 | 38 | 0 | 0 |

As can be seen from the above test, the surfactant increased the phytotoxicity of the compound with respect to 3-inch beggarweed and was still completely safe with respect to peanuts.

Obviously, many modifications and variations of the invention, described hereinabove and below, can be made without departing from the essence and scope thereof.

What is claimed is:

1. A method for providing preemergence herbicidal weed control in a crop selected from the group consisting of cotton, peanuts, peas, and sorghum which comprises applying to the habitat soil of said crop, within 7 days before the planting of seeds of said crop up to 3 days after planting, an amount which is effective to destroy or suppress weeds and is safe with respect to said crop, of a compound or mixture of compounds selected from the group having the formula:

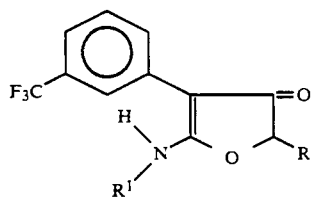

(I)

wherein R is phenyl; $R^1$ is methyl or ethyl; and compatible salts thereof.

2. The method of claim 1 wherein said compound is applied up to and including the time of cracking of the soil by said weeds.

3. The method of claim 1 wherein $R^1$ is methyl.

4. The method of claim 1 wherein said weeds are broadleaf weeds.

5. The method of claim 1 wherein said compound is applied within 2 days before planting of said crop up to 2 days after planting of said crop.

6. The method of claim 1 wherein said crop is selected from the group consisting of peanuts and cotton.

7. A method for providing preemergence herbicidal weed control in a crop selected from the group consisting of peanuts and non-western cotton which comprises applying to the habitat of said crop within 7 days before planting seeds of said crop up to 3 days after planting said crop, an amount which is effective to suppress or destroy weeds and is safe with respect to said crop, of a compound, or mixture of compounds, selected from the group having the formula:

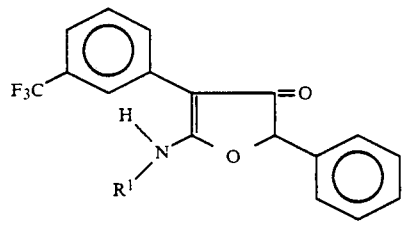

wherein $R_1$ is methyl or ethyl; and compatible salts thereof.

8. The method of claim 7 wherein said weeds are broadleaf weeds.

9. The method of claim 7 which comprises applying said amount of compound in two or more applications which are applied on the same day or within one day of each other.

10. The method of claim 7 wherein said compound is applied within 2 days before planting of said crop up to 2 days after planting of said crop.

11. The method of claim 7 wherein said crop is peanuts.

12. The method of claim 7 wherein an amount in the range of about from 0.15 to 1.5 lbs of said compound is applied per acre.

13. The method of claim 12 wherein said crop is peanuts and wherein said amount is in the range of about from 0.5 to 1 lb of said compound per acre.

14. The method of claim 12 wherein $R^1$ is methyl.

15. The method of claim 7 wherein $R^1$ is methyl.

16. The method of claim 15 wherein said crop is peanuts.

17. The method of claim 16 wherein said weeds include broadleaf weeds.

* * * * *